(12) United States Patent
Small et al.

(10) Patent No.: US 6,969,849 B2
(45) Date of Patent: Nov. 29, 2005

(54) MASS SPECTROMETER FOR ENTRAINED PARTICLES, AND METHOD FOR MEASURING MASSES OF THE PARTICLES

(75) Inventors: James G. Small, Tucson, AZ (US); Jon N. Leonard, Tucson, AZ (US)

(73) Assignee: Raytheon Company, Waltham, MA (US)

( * ) Notice: Subject to any disclaimer, the term of this patent is extended or adjusted under 35 U.S.C. 154(b) by 86 days.

(21) Appl. No.: 10/685,830

(22) Filed: Oct. 14, 2003

(65) Prior Publication Data

US 2005/0077463 A1 Apr. 14, 2005

(51) Int. Cl.[7] ............................................. H01J 49/00
(52) U.S. Cl. ................. 250/288; 250/423 R; 73/24.02; 356/51; 356/437
(58) Field of Search ........................... 250/288, 423 R; 73/24.02; 356/51, 437

(56) References Cited

U.S. PATENT DOCUMENTS

| 3,561,253 A | 2/1971 | Dorman |
| 3,844,174 A | 10/1974 | Chabre |
| 4,571,079 A | 2/1986 | Knollenberg |
| 5,742,050 A | 4/1998 | Amirav |
| 6,202,470 B1 * | 3/2001 | Chou ......................... 73/24.02 |
| 6,363,772 B1 * | 4/2002 | Berry ......................... 73/24.02 |
| 6,768,108 B2 * | 7/2004 | Hirano et al. ................ 250/288 |

FOREIGN PATENT DOCUMENTS

GB 2-335-491 9/1999

* cited by examiner

*Primary Examiner*—Nikita Wells
*Assistant Examiner*—Zia R. Hashmi
(74) *Attorney, Agent, or Firm*—Thomas J. Finn; Leonard A. Alkov; Karl A. Vick

(57) ABSTRACT

A particle mass spectrometer includes a supersonic flow expansion nozzle, and a source of a gas having particles entrained therein. The source is in gas-flow communication with an inlet of the expansion nozzle. The particle mass spectrometer further includes a vacuum chamber in gas-flow communication with an outlet of the expansion nozzle, wherein the vacuum chamber has a sufficient vacuum that a gas flow through the expansion nozzle is supersonic, and a microphone having an active element and an output signal responsive to a movement of the active element. The active element is disposed within the vacuum chamber and is positioned so that particles that flow from the outlet of the expansion nozzle impact upon the active element. The output signal of the active element of the microphone is a measure of the masses of the entrained particles.

20 Claims, 4 Drawing Sheets

Figure 1:
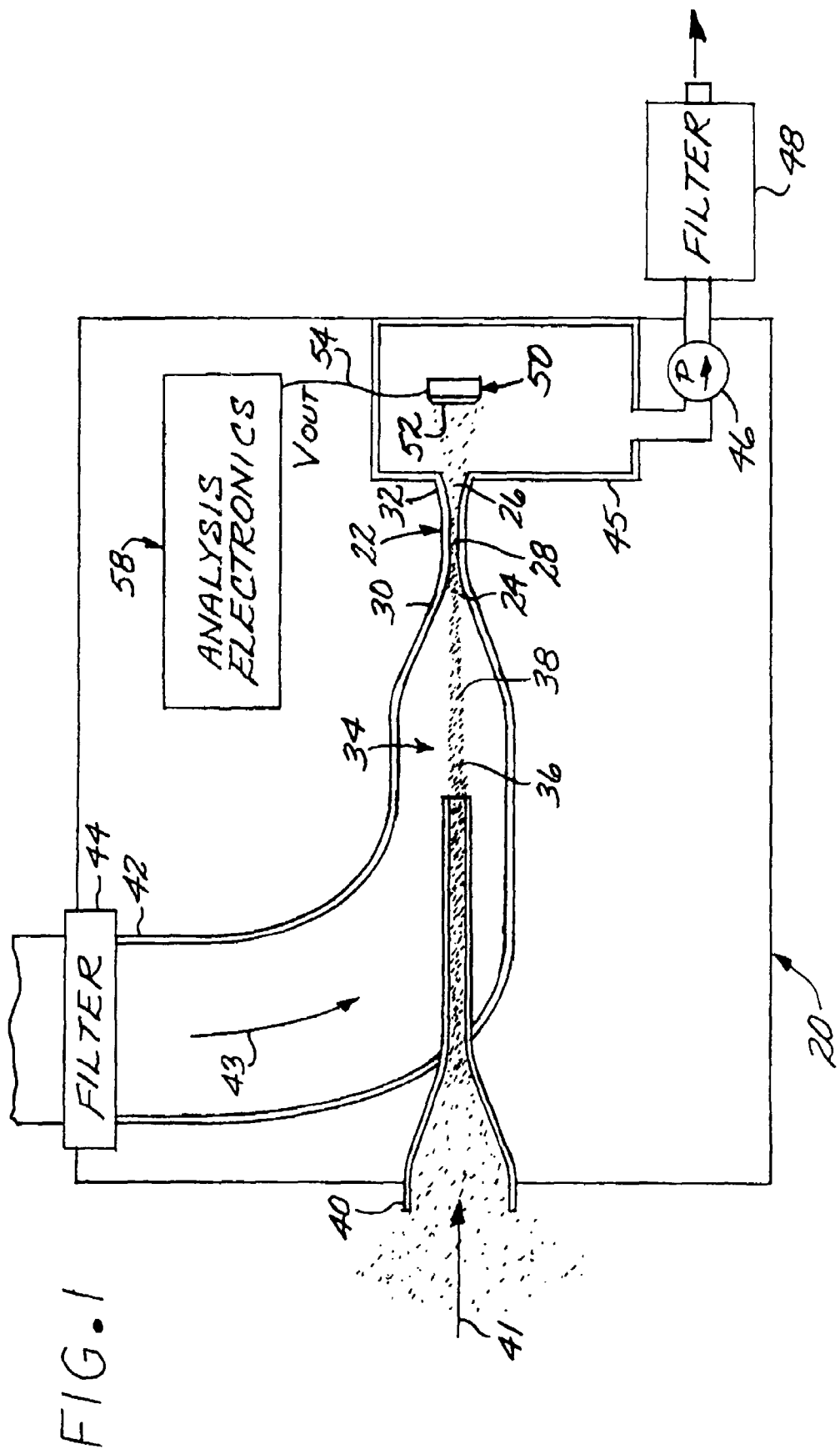

MASS SPECTROMETER FOR ENTRAINED PARTICLES, AND METHOD FOR MEASURING MASSES OF THE PARTICLES

This invention relates to the measurement of the masses of small particles and, more particularly, to a mass spectrometer that entrains the particles in a supersonic gas flow and impacts the particles on an active element of a microphone.

BACKGROUND OF THE INVENTION

It is important to identify precisely the nature of certain types of small particles. For example, various biologically active species such as different types of viruses have widely varying effects on living organisms. Some may have little effect, and others may be deadly. Persons who are potentially exposed to viruses need an accurate approach to rapidly and accurately identify the nature of such viruses, so that preventative measures or countermeasures may be employed as necessary. In other cases no action need be taken with viruses that are not potentially injurious.

A number of chemical and physical techniques are useful for identifying small particles such as viruses. Chemically active small particles may be analyzed by observing their chemical reactivity. In one technique, the particles are captured in a filter and then chemically tested by determining their reactivity with other species or with particular chemicals. Such chemical testing may be quite slow in providing an identification, however. Small particles may also be analyzed according to physical properties, such as by X-ray diffraction to determine their internal structure. This approach also requires a considerable time and also cannot be performed readily on small numbers of very small particles. Small particles may also be captured and visually analyzed to estimate their masses, using a powerful microscope such as a scanning electron microscope. This technique does not yield information in real time, and it requires the availability of a scanning electron microscope.

In another approach which is used to analyze larger particles and has the potential for real-time analysis, a light beam is passed through an entrained flow of the particles. The scattered light beam is used to obtain a distribution of sizes of the particles, which may be approximately related to a distribution of particle masses. However, light scattering is not useful to detect particles which are much smaller than the wavelength of light, as is the case for viral particles.

There is therefore a need for an approach to rapidly and accurately analyzing for the presence and nature of small particles in the atmosphere and elsewhere. The present invention fulfills this need, and further provides related advantages.

SUMMARY OF THE INVENTION

The present invention provides an apparatus and method for measuring the masses of small particles that are entrained in a gas flow. The approach allows the rapid measurement of the masses of very small particles, such as viruses. There is substantially no delay between the time when the particles are encountered and the time when the mass information is available. For viruses, the mass information correlates well with the nature of the virus, so that the nature of the virus may be determined essentially instantaneously.

A knowledge of the mass of a small particle may be useful in identifying the nature of the particle. Viruses typically have characteristic masses. That is, the mass of each particle of a particular type of virus is substantially the same, as the virus does not grow or fragment during its life, unlike a bacterium where the mass changes over time and there may be a range of masses for each type of bacterium, and unlike other types of particles which do not have discrete masses. The characteristic virus masses are smaller than the masses of almost all other types of particles that are routinely encountered.

In accordance with the invention, a particle mass spectrometer comprises a supersonic flow expansion nozzle having an inlet and an outlet, and a source of a gas having particles entrained therein. The expansion nozzle is preferably a converging-diverging expansion nozzle. The particles may be viruses with a mass of from about $10^6$–$10^{10}$ Daltons. The source is in gas-flow communication with the inlet of the expansion nozzle.

The particle mass spectrometer further includes a vacuum chamber in gas-flow communication with the outlet of the expansion nozzle. The vacuum chamber has a sufficiently low pressure, typically in the range of from about $10^{-3}$ Torr to about $10^{-1}$ Torr, that a gas flow through the expansion nozzle is supersonic. Pressures below $10^{-3}$ Torr are acceptable, but it is preferred that the pressure not be greater than $10^{-1}$ Torr so that the mean free path of the gas molecules is long.

A microphone has an active element and an output signal responsive to a movement of the active element. The active element typically moves in response to the impact by the particles. The active element of the microphone is preferably either a piece of a piezoelectric material or a flexible diaphragm. The active element is disposed within the vacuum chamber and is positioned so that particles that flow from the outlet of the expansion nozzle impact upon the active element. The output signal of the microphone is an indicator of the masses of the individual particles impacting upon the active element.

In some cases, the flow of particles to the active element of the microphone may be so great that the output signals associated with the individual particles overlap and cannot be readily analyzed. The particles may be angularly spread out to aid in the analysis, as by electrostatically deflecting the particles. A set of electrostatic deflection plates is disposed so that the particles that flow from the outlet of the expansion nozzle toward the microphone must pass between the deflection plates and are deflected. The electrostatically deflected particles impact upon an array of microphones. Each microphone of the array has an active element and an output signal responsive to a movement of the active element. Each active element is disposed within the vacuum chamber and positioned so that particles that flow from the outlet of the expansion nozzle impact upon the active element. The electrostatically deflected particles are laterally spread out so as to impact different ones of the active elements of the microphones, thereby reducing the particle impacts for each individual microphone and reducing the overlap in signals to make analysis easier.

A method for determining the masses of particles comprises the steps of entraining the particles in a flow of gas, passing the flow of gas with the particles entrained therein through a supersonic flow expansion nozzle into a vacuum, and impacting the flow of gas with the particles entrained therein on an active element of a microphone that is maintained within the vacuum, after the flow of gas with the particles entrained therein leaves the expansion nozzle. The output signal of the microphone is associated with the masses of the particles. Other compatible features discussed herein, such as the electrostatic deflection plates and the array of microphones, may be used in relation to the method.

Figure 2:
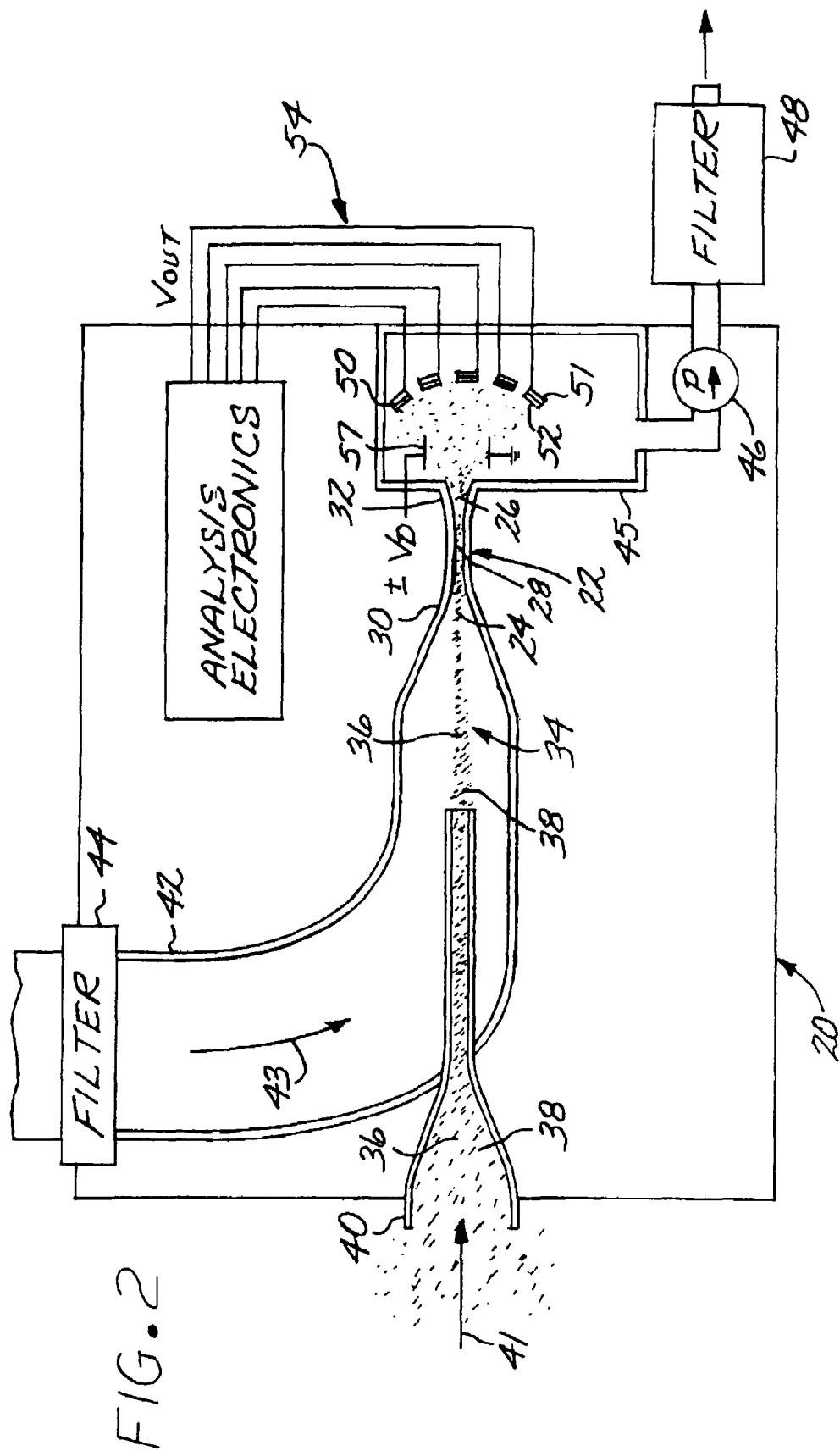
Figure 3:
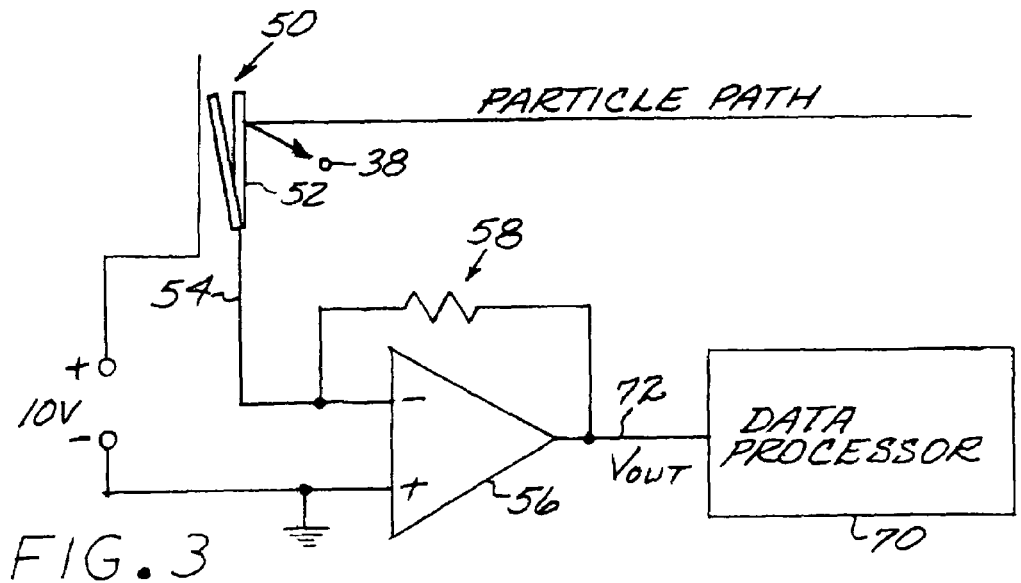

The present approach essentially instantaneously determines the masses of particles entrained in a gas flow and supplied to the apparatus. In some cases, such as for some viruses, the masses are directly associated with the nature of the virus particles, which in turn are associated with the chemical and/or biological properties and effects of the virus particles. The present approach thus provides a technique for instantaneously determining the type, and the chemical and/or biological nature of such particles.

Other features and advantages of the present invention will be apparent from the following more detailed description of the preferred embodiment, taken in conjunction with the accompanying drawings, which illustrate, by way of example, the principles of the invention. The scope of the invention is not, however, limited to this preferred embodiment.

BRIEF DESCRIPTION OF THE DRAWINGS

FIG. 1 is a schematic drawing of a first embodiment of a particle mass spectrometer;

FIG. 2 is a schematic drawing of a second embodiment of the particle mass spectrometer;

FIG. 3 is a schematic illustration of the microphone and the analysis electronics;

FIG. 4 is a schematic illustration of the output signal of the microphone for two particles of different masses;

FIG. 5 is a graph of frequency of occurrence as a function of the reciprocal of the particle mass, in the output signal of the microphone; and FIG. 6 is a block flow diagram of an approach for practicing a preferred embodiment of the method of the invention.

DETAILED DESCRIPTION OF THE INVENTION

FIGS. 1 and 2 illustrate two embodiments of a particle mass spectrometer 20. The two embodiments are the same, except as will be discussed. In each case the particle mass spectrometer 20 includes a supersonic flow expansion nozzle 22 having an inlet 24 and an outlet 26. The expansion nozzle 22 is preferably a converging-diverging expansion nozzle, having a narrow throat 28, a converging region 30 of decreasing cross-sectional area from the inlet 24 to the throat 28, and a diverging region 32 of increasing cross-sectional area from the throat 28 to the outlet 26.

There is a source 34 of a gas 36 having particles 38 entrained therein that is in gas-flow communication with the inlet 24 of the expansion nozzle 22. The pictured source 34 includes a sample inlet 40 and an optional dilutent inlet 42. The particles 38 in a sample gas flow 41 are drawn into the sample inlet 40 to serve as a sample. The sample gas flow is optionally mixed with a dilutent gas flow 43 that is first filtered through a filter 44 and drawn into the dilutent inlet 42, to create the source 34 of the gas 36 having the particles 38 therein. The gas 36 is typically air, but it may be any operable gas. The gas flow from the sample inlet 40 is preferably diluted with the dilutent gas flow 43 from the dilutent inlet 42 to reduce the number density of the particles 38 in the gas source 34 and thence reduce the possible overlaps in the measured output signal to be discussed subsequently. Otherwise, the high mass flow of the particles and the resulting signal overlap may obscure important information. The relative flow rates of the sample and the dilutent are used to calculate back to the density of particles in the sample.

The particles 38 may be of any type operable with the present approach, and may have a wide range of particle masses. Typically, there is a wide range of particle masses in any sampling. A preferred application of the present approach is to analyze samples that may have virus particles 38 therein. The mass of individual virus particles is typically from about $10^6$ to about $10^{10}$ Daltons, depending upon the type of virus, which is quite small compared to the mass of a bacterium, a dust particle, or a soot particle, but large compared to the mass of an air molecule or many types of aromatic organic molecules. The mass of a virus particle is a good indicator of the type of virus, since the particles of any one type of virus have essentially the same mass because the virus particles do not grow or fragment over time.

A vacuum chamber 45 is in gas-flow communication with the outlet 26 of the expansion nozzle 22. The vacuum chamber 45 is pumped by a vacuum pump 46 that exhausts through a filter 48. The vacuum chamber 45 and the pump 46 are sized so that, considering the provided gas flow rate from the source 34 (i.e., the sum of the sample gas flow 41 and the dilutent gas flow 43), the vacuum chamber has a sufficient vacuum that a gas flow through the expansion nozzle 22 is supersonic. In a typical case, the vacuum chamber 45 has a pressure of from about $10^{-3}$ Torr to about $10^{-1}$ Torr, most preferably about $10^2$ Torr. A substantially higher pressure in the vacuum chamber 45 will not produce a supersonic gas flow through the expansion nozzle 22. A vacuum in communication with the outlet 26 of the expansion nozzle 22 must be used to provide the driving force for the gas flow through the expansion nozzle 22. A positive pressure applied to the inlet 24, without a sufficiently high vacuum communicating with the outlet 26, may not be used. The vacuum on the outlet side is necessary to reduce the mean free path for molecular collisions so that a shock wave does not build up that prevents the supersonic flow.

A microphone 50, also shown in FIG. 3 in more detail, has an active element 52 and an output signal 54 responsive to a movement of the active element 52. When particles 38 impact the active element 52, the pressure associated with each individual particle impact produces the electrical (or optical) output signal 54 from the active element 52, as the active element deflects. The output signal 54 is amplified by an amplifier 56 (FIG. 3) in an analysis electronics 58 to produce an output $V_{OUT}$. The active element 52 may be of any operable type, such as a flexible diaphragm in a capacitance microphone as illustrated in FIG. 3, or a piezoelectric material. The active element 52 of the microphone 50 is disposed within the vacuum chamber 45 and is positioned so that particles 38 that flow from the outlet 26 of the expansion nozzle 22 impact upon the active element 52.

An important feature of the present approach is the achieving of a supersonic velocity of the gas 36 and particles 38 that flow through the supersonic flow expansion nozzle 22. When the gas 36 moves at a supersonic velocity, the particles 38 move at a supersonic velocity. The particles 38 have comparable velocities (ideally exactly the same velocities), regardless of their masses. The momentum and pressure of the impact of each particle 38 on the active element 52 is therefore largely a function only of the mass of the particle 38, and is generally proportional to the mass of the particle. Thus, the pulsed output signal 54 for each particle impact is largely a function of the mass of the impacting particle 38.

The embodiments of FIGS. 1 and 2 differ in that the particle mass spectrometer 20 of FIG. 1 has a single microphone 50, and the particle mass spectrometer 20 of FIG. 2 has an array 51 of a plurality of microphones 50. The particle mass spectrometer of FIG. 2 also includes a set of electrostatic deflectors, here electrostatic deflection plates 57, disposed such that the particles 38 that flow from the outlet 26 of the expansion nozzle 22 toward the microphone 50 must pass between the deflection plates 57. A voltage $V_D$, typically on the order of 500–1000 volts, is applied between the electrostatic deflection plates 57. The particles 38 are charged as they pass through the expansion nozzle 22 and are deflected slightly by the electrostatic deflection plates 57 according to their respective masses and charges. This causes particles 38, even particles of identical masses, to be deflected by slightly different amounts to impact different ones of the microphones 50 of the array. The angular and spatial separation is not the spectrometer effect (and therefore the deflection plates 57 are not necessary for practicing the present approach), but instead simply reduces the flux of particles 38 to any one of the microphones 50 to reduce the signal rate in the output signal 54. The dilution of the sample by the dilutent gas flow 43 has largely the same effect. This reduction in signal rates ensures that the effect of each individual particle 38 is clearly distinguishable in the output signal 54, and avoids superposition of the signals of the individual particles 38. Deflection plates 57 may also be used with the embodiment of FIG. 1.

Figure 4:
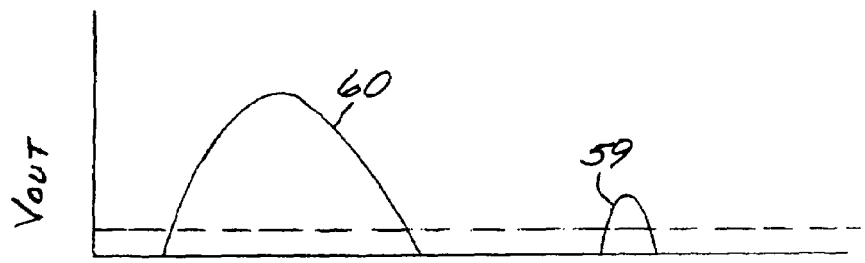

FIG. 4 illustrates the output signal $V_{OUT}$ of two different particles striking the active element 52. A smaller particle has an output signal 59 with a smaller integrated area than a larger particle with an output signal 60.

Figure 5:
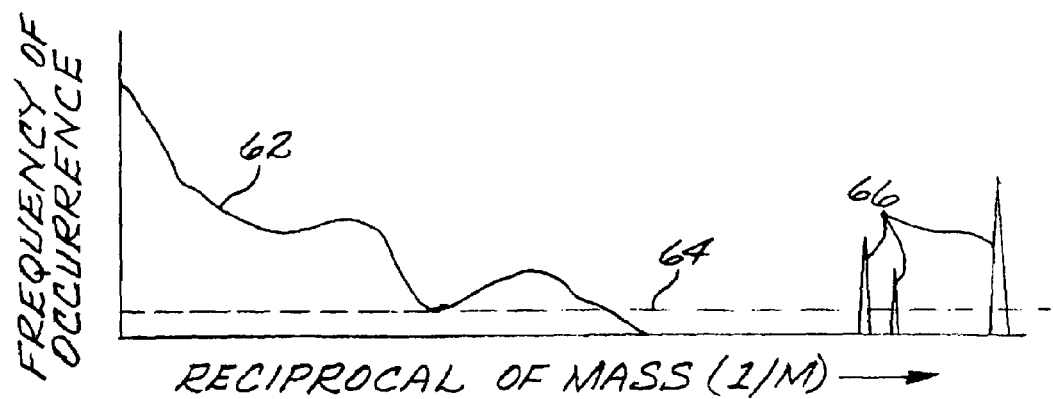

In operation, a large number of particles may be measured and the results combined in a frequency-mass distribution as shown in FIG. 5. For the particles of larger masses (smaller reciprocal masses), there is typically a continuous distribution 62 of frequencies of occurrence above a background level 64, because larger particles normally do not correspond to discrete masses. That is, a larger particle such as a dust particle or a soot particle typically does not have a specific mass—there are usually dust and soot particles of a variety of masses. For the particles of smaller masses, such as virus particles, there are typically discrete peaks 66 in the distribution because the only particles in that mass range are the specific types of particles such as viruses in which the mass of each virus particle is the same as the mass of each other virus particle of the same type. These discrete peaks 66 may therefore often be associated with different specific types of particles 38, such as specific types of virus particles.

To assist in identifying the nature of the small particles, the analysis electronics 58 may further include an optional data processor 70 that receives the amplified output signal ($V_{OUT}$) 72 as shown, or the unamplified output signal 54, and analyzes the output signal 72 or 54. The analysis performed in the data processor 70 may be of any relevant type, but typically associates the output signal with the known masses of particular particle types. In the case of interest where the small particles are viruses, the data processor 70 may contain a lookup table of virus mass as a function of the virus type, and the peaks 66 in the output signal may be associated with these virus types.

The data processor 70 may also serve to compensate for any velocity nonuniformities in the particles 38 that pass through the expansion nozzle 22. That is, if one type of small particle always moves at a greater velocity than another type of small particle, so that the momentum impact on the active element 52 is not proportional solely to the mass of the particles, the lookup table may take this effect into account by being based on a parameter that is not purely mass, but instead takes into account the velocity dependence as well. Such an approach is implemented by performing calibration studies wherein measurements are serially performed on the source gas 34 that controllably includes only a single type of a known small particle at a time.

Figure 6:
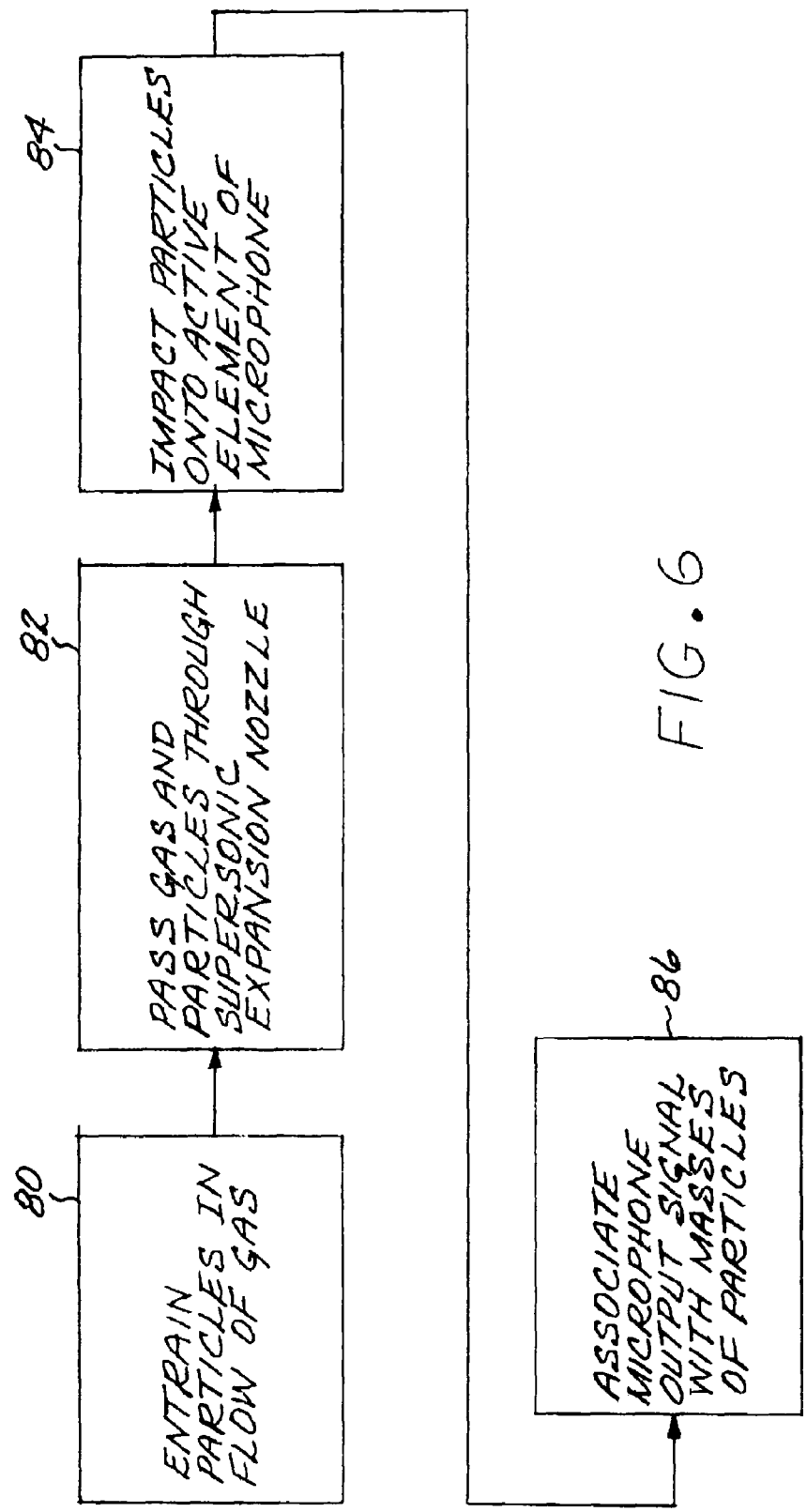

FIG. 6 depicts a method for determining the masses of particles. The method involves entraining the particles in a flow of gas, step 80, and passing the flow of gas 36 with the particles 38 entrained therein through the supersonic-flow expansion nozzle 22 into a vacuum, step 82. The flow of gas 36 with the particles 38 entrained therein is impacted on the active element 52 of the microphone 50 (either a single microphone 50 or an array 51 of microphones 50) that is maintained within the vacuum, after the flow of gas 36 with the particles 38 entrained therein leaves the expansion nozzle, step 84. The output signal 54 of the microphone 50 is associated with the masses of the particles 38, step 86. The association step 86 may include forming relations such as shown in FIGS. 4 and 5, including but not limited to performing calibration studies to associate particular masses of the particles with specific types of viruses. Other operable features of the present approach, as discussed herein, may be utilized in relation to the method.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. A particle mass spectrometer, comprising:
    a supersonic flow expansion nozzle having an inlet and an outlet;
    a source of a gas having particles entrained therein, wherein the source is in gas-flow communication with the inlet of the expansion nozzle;
    a vacuum chamber in gas-flow communication with the outlet of the expansion nozzle, wherein the vacuum chamber has a sufficient vacuum that a gas flow through the expansion nozzle is supersonic; and
    a microphone having an active element and an output signal responsive to a movement of the active element, wherein the active element is disposed within the vacuum chamber and is positioned so that particles that flow from the outlet of the expansion nozzle impact upon the active element.

2. The particle mass spectrometer of claim 1, wherein the expansion nozzle is a converging-diverging expansion nozzle.

3. The particle mass spectrometer of claim 1, wherein the source of the gas comprises
    a source of particles having a mass of from about $10^6$–$10^{10}$ Daltons.

4. The particle mass spectrometer of claim 1, wherein the source of the gas comprises
    a source of virus particles.

5. The particle mass spectrometer of claim 1, wherein the vacuum chamber has a pressure of from about $10^{-3}$ Torr to about $10^{-1}$ Torr.

6. The particle mass spectrometer of claim 1, wherein the active element of the microphone comprises a piece of a piezoelectric material.

7. The particle mass spectrometer of claim 1, wherein the active element of the microphone comprises a flexible diaphragm.

8. The particle mass spectrometer of claim 1, further including
   a set of electrostatic deflection plates disposed such that particles that flow from the outlet of the expansion nozzle toward the microphone must pass between the deflection plates.

9. The particle mass spectrometer of claim 1, wherein the microphone comprises
   an array of microphones.

10. The particle mass spectrometer of claim 1, further including
    a data processor that receives the output signal and associates the output signal with particle types.

11. A particle mass spectrometer, comprising:
    a supersonic flow, converging/diverging expansion nozzle having an inlet and an outlet;
    a source of a gas having particles entrained therein, wherein the source is in gas-flow communication with the inlet of the expansion nozzle;
    a vacuum chamber in gas-flow communication with the outlet of the expansion nozzle, wherein the vacuum chamber has a sufficient vacuum that a gas flow through the expansion nozzle is supersonic;
    an array of microphones, each microphone having an active element and an output signal responsive to a movement of the active element, wherein each active element is disposed within the vacuum chamber and positioned so that particles that flow from the outlet of the expansion nozzle impact upon the active element; and
    a set of electrostatic deflection plates disposed such that particles that flow from the outlet of the expansion nozzle toward the array of microphones must pass between the deflection plates.

12. The particle mass spectrometer of claim 11, wherein the source of the gas comprises
    a source of particles having a mass of from about $10^6$–$10^{10}$ Daltons.

13. The particle mass spectrometer of claim 11, wherein the source of the gas comprises
    a source of virus particles.

14. The particle mass spectrometer of claim 11, wherein the vacuum chamber has a pressure of from about $10^{-3}$ Torr to about $10^{-1}$ Torr.

15. A method for determining a mass of particles, comprising the steps of
    entraining the particles in a flow of gas;
    passing the flow of gas with the particles entrained therein through a supersonic-flow expansion nozzle into a vacuum;
    impacting the flow of gas with the particles entrained therein on an active element of a microphone that is maintained within the vacuum, after the flow of gas with the particles entrained therein leaves the expansion nozzle; and
    associating an output signal of the microphone with the masses of the particles.

16. The method of claim 15, wherein the step of entraining includes the step of
    providing particles having a mass of from about $10^6$–$10^{10}$ Daltons.

17. The method of claim 15, wherein the step of entraining includes the step of
    providing a source of virus particles.

18. The method of claim 15, wherein the step of passing includes the step of
    providing the vacuum with a pressure of from about $10^{-3}$ Torr to about $10^{-1}$ Torr.

19. The method of claim 15, wherein the method includes an additional step of
    electrostatically deflecting the particles entrained in the flow of gas leaving the supersonic flow expansion nozzle.

20. The method of claim 15, wherein the step of impacting includes the step of
    providing an array of microphones, and
    wherein the method includes an additional step of
    electrostatically deflecting the particles entrained in the flow of gas leaving the supersonic flow expansion nozzle so that the particles impact one of the microphones in the array of microphones.

\* \* \* \* \*